United States Patent [19]

Meyer et al.

[11] Patent Number: 5,230,701
[45] Date of Patent: Jul. 27, 1993

[54] ELASTOMERIC ADHESIVE AND COHESIVE MATERIALS

[75] Inventors: Daniel E. Meyer; John E. Riedel, both of St. Paul, Minn.

[73] Assignee: Minnesota Mining and Manufacturing Company, St. Paul, Minn.

[21] Appl. No.: 841,890

[22] Filed: Feb. 25, 1992

Related U.S. Application Data

[63] Continuation of Ser. No. 697,724, May 3, 1991, abandoned, which is a continuation of Ser. No. 433,394, Nov. 7, 1989, abandoned, which is a continuation of Ser. No. 193,906, May 13, 1988, abandoned.

[51] Int. Cl.$^5$ .............................................. A01L 15/00
[52] U.S. Cl. .................................... 602/76; 602/903; 602/54; 602/58; 428/230
[58] Field of Search ................................ 602/75-77, 602/385.2, 903, 54-58; 428/221, 224, 230, 288, 903

[56] References Cited

U.S. PATENT DOCUMENTS

| | | | |
|---|---|---|---|
| 3,575,782 | 4/1971 | Hansen | 161/141 |
| 3,670,731 | 6/1972 | Harmon | 128/284 |
| 4,100,324 | 7/1978 | Anderson et al. | 428/288 |
| 4,118,531 | 10/1978 | Hauser | 428/224 |
| 4,209,563 | 6/1980 | Sisson | 428/288 |
| 4,366,814 | 1/1983 | Riedel | 128/156 |
| 4,379,192 | 4/1983 | Wahlquist et al. | 428/156 |
| 4,414,970 | 11/1983 | Berry | 128/156 |
| 4,565,736 | 1/1986 | Stein et al. | 428/286 |
| 4,650,479 | 3/1987 | Insley | 604/358 |
| 4,652,487 | 3/1987 | Morman | 428/138 |
| 4,653,492 | 3/1987 | Parsons | 128/155 |
| 4,660,228 | 4/1987 | Ogawa et al. | 2/167 |
| 4,663,220 | 5/1987 | Wisneski et al. | 428/221 |
| 4,692,368 | 9/1987 | Taylor et al. | 428/137 |
| 4,692,371 | 9/1987 | Morman et al. | 428/224 |
| 4,699,133 | 10/1987 | Schafer et al. | 128/156 |
| 4,707,398 | 11/1987 | Boggs | 428/224 |
| 4,715,857 | 12/1987 | Juhasz et al. | 604/359 |
| 4,741,949 | 5/1988 | Morman et al. | 428/324 |
| 4,823,427 | 4/1989 | Gibbs et al. | 15/247 |

FOREIGN PATENT DOCUMENTS

| | | |
|---|---|---|
| 0156649 | 8/1981 | European Pat. Off. . |
| 0080008 | 6/1983 | European Pat. Off. . |
| 0258484 | 3/1988 | European Pat. Off. . |
| 1575830 | 6/1971 | United Kingdom . |

OTHER PUBLICATIONS

Wente, Van A.-Superfine Thermoplastic Fibers *Ind. Eng. Chem.* vol. 48, pages 1342 et seq. (1956).

Development of Spunbonded Based on Thermoplastic Polyurethane *Nonwoven World*, May-Jun., 1986 pp. 79-81.

Report 4364 Naval Res. Labs, May 25, 1954 Manufacture of Superfine Organic Fibers by Wente, Van A., Boone, C. D. & Fhuharty, E. L.

*Primary Examiner*—Randall L. Green
*Assistant Examiner*—K. M. Reichle
*Attorney, Agent, or Firm*—Gary L. Griswold; Walter N. Kirn; Thomas E. Jurgensen

[57] ABSTRACT

A nonwoven elastomeric web is provided. The web comprises thermoplastic elastomeric melt-blown small diameter fibers having a diameter of less than about 50 microns, the small diameter fibers being randomly arrayed and bonded at points of contact such that the tensile strength of the web in the direction of web formation is no greater than about 2.5 times the tensile strength of the web in a direction perpendicular to the direction of web formation and the web recovers at least about 85% in the machine direction after being stretched 50%. The web is particularly useful as wound dressing or bandaging materials.

10 Claims, No Drawings

ELASTOMERIC ADHESIVE AND COHESIVE MATERIALS

This is a continuation of application Ser. No. 07/697,724, filed May 3, 1991 which is a continuation of application Ser. No. 07/433,394, filed Nov. 7, 1989 which is a continuation of application Ser. No. 07/193,906, filed May 13, 1988 all now abandoned.

BACKGROUND OF THE INVENTION

1. Field of the Invention

The present invention relates to nonwoven elastomeric webs and to elastomeric adhesive and cohesive materials which are useful as wound dressing or bandaging materials.

2. Background Information

Dressings and tapes applied to the skin should preferably exhibit a degree of stretchiness so that they do not unduly restrict movement of the underlying skin. This is particularly important in skin areas such as fingers, elbows and knees which are subjected to continuous stretching and relaxation during normal activities. If a tape does not exhibit elastic properties similar to or greater than skin, the tape will exert a force against the skin causing discomfort and in some cases, actual damage to the skin.

Cohesive, self-adhesive compression and support bandages applied to limbs of the body are required to be elastic to provide variable tensions dependent on application and compensate for edemic conditions. After being wrapped on a limb some elasticity should remain in the bandage to allow for subsequent edema in the limb and the bandage should have sufficient elastic recovery to return to substantially the extensibility at application after the edema subsides.

U.S. Pat. No. 3,575,782 (Hansen) discloses an elastic shirred web product which consists of partially extended spaced aligned elastic yarns sealed between two thin porous gathered non-woven fibrous webs, or between a web and a non-porous film, by means of a soft flexible polymeric coherent binder.

U.S. Pat. No. 4,366,814 (Riedel) discloses an elastic bandage material for medical tapes and dressing which has at least 50 percent by weight of an extensible porous fabric capable of elongation of at least 30 percent in one direction without tearing and at least 15 percent by weight of an elastomer uniformly impregnated in the fabric and substantially contained on or within the fibers of the fabric without filling the spaces between fibers. The fabric may be of a wide range of synthetic or natural fibers, used singly or in blends. The preferred elastomers include block copolymers, polyurethanes, acrylics, acrylic-olefinic copolymers, and other natural and synthetic rubbers.

U.S. Pat. No. 4,414,970 (Berry) discloses a moisture vapor transmitting elastic bandage which has an inner layer of fabric and an outer layer of fabric bonded to a central layer which is an elastomeric film. The film can be continuous, macroporous or microporous, but is preferably continuous to provide a bacterial barrier. Suitable films which may be obtained in continuous form and which transmit moisture vapor can be made from polyurethane, for example, a thermoplastic polyurethane.

U.S. Pat. No. 4,565,736 (Stein et al.) discloses a surgical compress which is made of an absorptive layer and a wound covering layer, the covering layer spun or otherwise made of nonwoven hydrophobic, hydrolysis-resistant, aliphatic polyurethane fibers, the covering layer preferably being autogenously bonded to the absorption layer by direct formation of tacky cover layer fibers on the absorption layer.

U.S. Pat. No. 4,715,857 (Juhasz et al.) disclose wound dressings which comprise, in order, a first layer of a permeable material, a layer of a semi-permeable, adhesive material, a charcoal cloth or felt, and a second layer of a permeable material, in which the three layers are substantially co-extensive and surround the charcoal cloth or felt, whereby the first layer of permeable material is bound to the cloth or felt and, around the cloth or felt, to the second layer of permeable material. The layers of permeable material are in the form of a fabric or film and may be of different or, preferably, the same material, examples of suitable materials being natural or synthetic rubber, nylon, polyester, polyurethane and rayon acetate, and other suitable synthetic polymers. The semi-permeable adhesive materials are preferably double-sided transfer tapes.

U.S. Pat. No. 4,653,492 (Parsons) discloses an elastic bandage having a resilient elastic layer and a relatively non-resilient layer. The elastic layer has sufficient resiliency so as to apply a compressive force to a body extremity when wrapped around the body extremity and the relatively non-resilient layer which has either less resiliency than the elastic layer or relatively little resiliency or no resiliency limits the stretching of the layer of elastic material so that an inexperienced person can apply the elastic bandage without fear of applying it too tightly or too loosely.

U.S. Pat. No. 4,699,133 (Schafer et al.) discloses a cohesive, self-adhesive, rigid or elastic bandage for fixing, compression and support dressings and permanent elastic compression and support dressings for medical purposes. The bandage comprises a web of warp and weft threads or warp threads in the form of a woven fabric having a porous structure and an amount of ultra fine particles of an adhesive, such as a rubber adhesive distributed over and bonded to both the exposed surfaces of the warp and weft threads to provide adhesive particles bonded to the threads on both sides of the fabric.

British Patent Specification 1,575,830 (Johnson & Johnson) discloses a flexible and conformable disposable absorbent dressing which comprises a layer of absorbent material, and a thin, flexible, elastic and easily stretchable thermoplastic backing film retained in superimposed relationship with the absorbent layer, the backing film possessing an elastic recovery from 50 percent stretch of at least 75 percent, a rubber modulus of not above 2000 pounds per square inch and a Gurley stiffness at a thickness of 1 mil of not above one. The film is preferably formed from A-B-A block copolymers which consist of A end blocks derived from styrene and B blocks derived from conjugated dienes.

Ogawa, in an article entitled "Development of Spunbonded Based on Thermoplastic Polyurethane," *Nonwovens World*, May–June, 1986. pp 79–81, describes a spunbonded nonwoven polyurethane elastic fabric developed by Kanebo Ltd. The fabric is made using a melt blown process which is different from a conventional melt blown process to produce fabric which is similar to that of spunbonded fabrics. The diameter of its filaments is not so fine as that of the usual melt blown fabrics, i.e., 0.5–2 mm, but apparently is closer to that of the spunbonded fabrics, i.e., 20–50 mm. The elasticity, dust catching capability, low linting, high friction coefficient, air permeability and welding characteristics of the urethane fabrics are discussed in the article.

SUMMARY OF THE INVENTION

The present invention provides a nonwoven elastomeric web comprising elastomeric melt blown small diameter fibers having a diameter of less than about 50 microns, the small diameter fibers being randomly arrayed and bonded at points of contact such that the tensile strength of the web in the direction of web formation, i.e., the machine direction, is no greater than about 2.5 times the tensile strength of the web in a direction perpendicular to the direction of web formation, i.e., the cross direction and the web recovers at least about 85% in the machine direction after being stretched 50%.

The invention further provides an adhesive dressing comprising (1) a nonwoven elastomeric web having a first face and a second face comprising elastomeric melt-blown small diameter fibers having a diameter of less than about 50 microns, the small diameter fibers being randomly arrayed and bonded at points of contact such that the tensile strength of the web in the direction of web formation is no greater than about 2.5 times the tensile strength of the web in a direction perpendicular to the direction of web formation and the web recovers at least about 85% in the machine direction after being stretched 50%, (2) a pressure-sensitive adhesive on the first face of the web, and (3) a low adhesion backsize coating on the second face of the web.

The present invention still further provides an elastomeric cohesive wrap comprising (1) a nonwoven elastomeric web having a first face and a second face comprising elastomeric melt blown small diameter fibers having a diameter of less than about 50 microns, the small diameter fibers being randomly arrayed and bonded at points of contact such that the tensile strength of the web in the direction of web formation is no greater than about 2.5 times the tensile strength of the web in a direction perpendicular to the direction of web formation and the web recovers at least about 85% in the machine direction after being stretched 50% and (2) a self-adhesive coating adhered to at least one face of the web such that one portion of the web can adhere to another portion of the web.

The elastomeric adhesive materials of the present invention have multi-directional elastic properties, i.e., substantially comparable properties in both the machine and cross-machine directions, the tensile strength of the web in the direction of web formation being no greater than about 2.5 times the tensile strength of the web in a direction perpendicular to the direction of web formation. Conventional wraps achieve multi-directional stretch properties only by using more expensive woven elastic fabrics which must have their edges securely anchored to prevent fiber slippage and subsequent loss of tensioning.

Both the adhesive and cohesive elastic materials find utility as an elastic bandage for fixing, compression support dressings for medical purposes. The unique ability of the bandage to stretch and recover in both directions allows for more uniform compression, greater patient comfort and less potential for unsafe use.

DETAILED DESCRIPTION OF THE INVENTION

The nonwoven elastomeric webs of the present invention are based on melt blown webs of thermoplastic elastomeric small diameter fibers. Elastomeric thermoplastic materials from which the microfiber webs can be prepared include, for example, elastomeric polyurethanes, elastomeric polyesters, elastomeric polyamides and elastomeric A-B-A' block copolymers wherein A and A' are styrenic moieties and B is an elastomeric midblock.

Elastic properties of the nonwoven webs are controlled by the size of the fiber making up the web and the basis weight of the web. The elastomeric small diameter fibers preferably have diameters of from about 1 micron to greater than 50 microns, more preferably from about 5 microns to about 30 microns. When the diameter of the small diameter fibers is less than 1 micron, the web may lack sufficient tensile strength. When the diameter of the small diameter fibers is greater than about 50 microns, the contact surface area for adhesive anchorage or cohesive material contact decreases. Specific applications and the tension or pressure required for those applications determines the most preferred microfiber diameter for a given application. Generally speaking, applications requiring low tension use webs having smaller diameter fibers while applications requiring higher tensions utilize webs having larger diameter fibers.

The basis weight of the nonwoven elastomeric web is also a major factor in controlling the elastic properties of the web. Higher basis weight webs are typically used for applications requiring higher tensions while lower basis weight webs are utilized for applications requiring low tensions. Web basis weights are preferably in the range of from about 15 to about 150 grams/m$^2$, more preferably in the range of from about 20 to about 70 gm/m$^2$. As was the case with the fiber diameter, the specific application will determine the optimum web basis weight.

The nonwoven elastomeric web of the invention preferably has a machine direction tensile strength of at least about 30 g/2.5 cm width/g/m$^2$ basis weight, more preferably at least about 40 g/2.5 cm width/g/m$^2$ basis weight. When the tensile strength is less than 15 g/2.5 cm width/g/m$^2$ basis weight, the web may tear when stretched.

The nonwoven elastomeric web of the invention preferably has an elongation at break of at least about 250%, more preferably at least about about 300%. When the elongation at break is less than about 100%, the web does not exhibit acceptable elastic characteristics.

The nonwoven elastomeric web of the invention preferably has a machine direction force at 50% elongation of at least about 5 g/2.5 cm width/g/m$^2$ basis weight, more preferably at least about 7 g/2.5 cm width/g/m$^2$ basis 3 weight. When the force at 50% elongation is less than about g/2.5 cm width/g/m$^2$ basis weight, the web does not exhibit desirable compression characteristics.

The nonwoven elastomeric web of the invention preferably has a recovery force at 50% elongation of at least about 1.2 g/2.5 cm width/g/m$^2$ basis weight, more preferably about 1.6 g/2.5 cm width/g/m$^2$ basis weight. If the recovery force at 50% elongation is less than 0.8 g/2.5 cm width/g/m² basis weight, the web exhibits insufficient recovery force for the intended application.

The nonwoven elastomeric web of the invention preferably recovers at least about 85%, more preferably at least about 90%, most preferably at least about 95%, in the machine direction after being stretched 50% and the web preferably recovers at least about 80%, more preferably at least about 85%, most preferably at least about 90%, in the cross direction after being stretched 50%.

The cohesive wraps of the invention can be prepared by applying a self-adhesive material such as natural rubber to the nonwoven elastomeric microfiber web of the invention. Other useful adhesives include acrylic copolymers, block copolymers, formulated rubbers, and multi-polymer blends, which are well-known in the art. The amount of self-adhesive material applied on the web is preferably in the range of about 15 to 75 weight percent of the web basis weight, more preferably about 25 to about 40 percent of the web basis weight. The adhesive materials can be applied to the web, for example, as latexes, solutions, or powders by a variety of coating techniques such as, for example, spraying, roll coating, or padding.

Alternatively, a material which will render the surface of the melt blown fibers self-tacky can be blended with the elastomeric thermoplastic material prior to melt blowing the fiber to produce the cohesive wrap in a single step. Such materials include, for example, block copolymers, acrylic polymers, tackifying resins and natural rubber.

The adhesive wraps of the invention can be prepared by applying a pressure-sensitive adhesive material to one face of the web and a low adhesion backsize material to the opposite face of the web. A variety of pressure-sensitive adhesives can be used, but acrylate-based pressure-sensitive adhesives are preferred because of their hypoallergenicity and gas permeability and particularly preferred are acrylate-based medical pressure-sensitive adhesives because of their skin adhesion properties. The pressure-sensitive adhesive can be applied on the nonwoven elastomeric microfiber web as a solution or a latex or, alternatively, the elastomeric web can be laminated to an adhesive film or collected directly on an adhesive film. The amount of adhesive applied on the web is preferably in the range of from about 30 to 60 weight percent of the web basis weight, more preferably from about 35 to about 50 percent of the web basis weight.

Suitable low-adhesion backsize materials for use in the elastomeric adhesive dressings including, for example, silicone-based, urethane-based, and perfluoropolyether-based materials. Generally, urethane-based materials are preferred as the low-adhesion backsize material because they exhibit proper release characteristics and hypoallergenicity. The amount of low-adhesion backsize applied on the web is preferably in the range of about 1 to 5 weight percent of the web basis weight, more preferably from about 2.5 to 4 percent of the web basis weight.

The nonwoven melt blown elastomeric webs can be prepared by a process similar to that taught in Wente, Van A., "Superfine Thermoplastic Fibers" in Industrial Engineering Chemistry, Vol.48, pages 1342 et seq (1965), or in Report No. 4364 of the Naval Research Laboratories, published May 25, 1954 entitled "Manufacture of Superfine Organic Fibers" by Wente, Van A., Boone, C. D. and Fluharty, E. L. except that a drilled die is preferably used. The thermoplastic elastomeric materials are extruded through the die into a high velocity stream of heated air which draws out and attenuates the fibers prior to their solidification and collection. The fibers are collected in a random fashion, such as on a perforated screen cylinder, prior to complete fiber solidification so that the fibers are able to bond to one another and form a coherent web which does not require additional binders. In forming the adhesive dressing or the cohesive wrap of the invention, the blown fibers can be collected directly on an adhesive film carried on a release liner. Specific physical characteristics of the web are achieved by properly balancing the polymer rheology, the fiber forming and collection phases of the process to achieve desired web properties.

This invention is further illustrated by the following examples, but the particular materials and amounts thereof recited in these examples, as well as other conditions and details, should not be construed to unduly limit this invention.

In the examples all parts and percentages are by weight unless otherwise specified. The following test methods were used for evaluation purposes in the examples:

Tensile strength: ASTM Test Method No. D1682-64 using a sample width of 2.5 cm, a gauge length of 2.5 cm, and a crosshead speed of 25 cm/min;

Elongation at break: ASTM Test Method No. D1682-64 using a sample width of 2.5 cm, a gauge length of 2.5 cm, and a crosshead speed of 25 cm/min;

Force at 50% elongation: INDA Standard Test 90-75 (R77);

Recovery force at 50% elongation: INDA Standard Test 90-75 (R77); and

% Recovery: INDA Standard Test 90-75 (R77).

Cohesive strength: The non-adhesive coated side of a 2.54 cm×2.54 cm sample of adhesive dressing is adhered to a 2.54 cm×2.54 cm face of each of two T-shaped aluminum blocks. The adhesive coated surfaces of the samples are brought into contact with each other and a 9 kg weight is placed on the contacting mounted samples for one minute. The legs of the blocks are placed in an Instron ™ tensile tester and pulled apart at a rate of 5 cm/min.

EXAMPLES 1–9

In Example 1, an elastomeric, nonwoven, melt-blown, microfiber web was prepared using thermoplastic elastomeric polyurethane polymer (PS 440-101, a polyesterurethane available from K. J. Quinn Co., Malden, Mass.) and a process similar to that described in Wente, Van A., "Superfine Thermoplastic Fibers" in Industrial Engineering Chemistry, Vol. 48, pages 1342 et seq (1965) or in Report No. 4364 of the Naval Research Laboratories, published May 25, 1964 entitled "Manufacture of Superfine Organic Fibers" by Wente, Van A., Boone, C. D., and Fluharty, E. L. except that the melt-blowing die had smooth surfaces orifices (10/cm) with a 5:1 length-to-diameter ratio. The die temperature was maintained at 220° C., the primary air temperature and pressure were, respectively, 230° C. and 150 kPa, (0.63 mm gap width), and the polymer throughput rate was 450 gm/hr/cm. The resulting web had a fiber size of 5–10 microns, a basis weight of 20 g/m², and a thickness of 0.08 mm.

In Examples 2–9, elastomeric, nonwoven, melt-blown, microfiber webs were prepared as in Example 1, except that the fiber size, basis weight and thickness of the webs was as set forth in Table I.

TABLE I

| Example | Fiber size (microns) | Web basis weight (g/m2) | Web thickness (mm) |
|---|---|---|---|
| 1 | 5-10 | 20 | 0.08 |
| 2 | 5-10 | 32 | 0.12 |
| 3 | 5-10 | 60 | 0.23 |
| 4 | 5-10 | 70 | 0.27 |
| 5 | 5-10 | 15 | 0.06 |
| 6 | 22-30 | 20 | 0.08 |
| 7 | 22-30 | 45 | 0.19 |
| 8 | 22-30 | 60 | 0.24 |
| 9 | 22-30 | 68 | 0.27 |

The tensile strength (TS), elongation at break (E-B), force at 50% elongation (F-50%), recovery force at elongation (RF-50%), and the percent recovery (R) were determined in both the machine direction and the cross direction. The results are set forth in Tables II and III.

TABLE II

| | | Machine Direction | | |
|---|---|---|---|---|
| Example | TS (g/2.5 cm) | E-B (%) | F-50% (g/2.5 cm) | RF-50% (g/2.5 cm) | R (%) |
| 1 | 820 | 400 | 160 | 37 | 95 |
| 2 | 1350 | 420 | 250 | 63 | 95 |
| 3 | 2680 | 440 | 450 | 120 | 95 |
| 4 | 3050 | 430 | 495 | 138 | 95 |
| 5 | 610 | 360 | 110 | 26 | 90 |
| 6 | 670 | 310 | 125 | 40 | 95 |
| 7 | 1600 | 315 | 310 | 85 | 95 |
| 8 | 2590 | 380 | 490 | 145 | 95 |
| 9 | 3400 | 400 | 480 | 160 | 95 |

TABLE III

| | | Cross Direction | | |
|---|---|---|---|---|
| Example | TS (g/2.5 cm) | E-B (%) | F-50% (g/2.5 cm) | RF-50% (g/2.5 cm) | R (%) |
| 1 | 380 | 390 | 74 | 28 | 80 |
| 2 | 620 | 410 | 120 | 40 | 85 |
| 3 | 1130 | 440 | 250 | 75 | 85 |
| 4 | 1410 | 430 | 290 | 94 | 90 |
| 5 | 340 | 340 | 58 | 21 | 80 |
| 6 | 400 | 360 | 70 | 30 | 85 |
| 7 | 950 | 350 | 145 | 62 | 90 |
| 8 | 1430 | 420 | 270 | 85 | 90 |
| 9 | 1800 | 430 | 310 | 100 | 95 |

As can be seen from the data in Tables II and III, there are minor difference between the two fiber sizes, but the major contributor to modifying the physical properties is the web weight.

EXAMPLES 10-15

In Examples 10-15, nonwoven elastomeric small diameter fibers webs were prepared as in Example 1 except that in Examples 10 and 11 the thermoplastic elastomeric polyurethane polymer used was PS 441-400 and in Examples 12-15, the thermoplastic elastomeric polyurethane polymer was PS 455-208, both polymers available from K. J. Quinn, Malden, Mass. The fiber size, web basis weight, and web thickness are set forth in Table IV.

TABLE IV

| Example | Fiber size (microns) | Web basis weight (g/m2) | Web thickness (mm) |
|---|---|---|---|
| 10 | 22-30 | 63 | 0.24 |
| 11 | 22-30 | 64 | 0.25 |
| 12 | 5-10 | 19 | 0.08 |
| 13 | 5-10 | 45 | 0.18 |
| 14 | 22-30 | 49 | 0.20 |
| 15 | 22-30 | 70 | 0.28 |

The tensile strength (TS), elongation at break (E-B), force at 50% elongation (F-50%), recovery force at 50% elongation (RF-50%), and the percent recovery (R) were determined in both the machine direction and the cross direction. The results are set forth in Tables V and VI.

TABLE V

| | | Machine Direction | | |
|---|---|---|---|---|
| Example | TS (g/2.5 cm) | E-B (%) | F-50% (g/2.5 cm) | RF-50% (g/2.5 cm) | R (%) |
| 10 | 2540 | 390 | 490 | 130 | 90 |
| 11 | 2470 | 400 | 490 | 135 | 90 |
| 12 | 730 | 430 | 135 | 30 | 95 |
| 13 | 1970 | 410 | 330 | 82 | 95 |
| 14 | 2410 | 420 | 390 | 105 | 95 |
| 15 | 3400 | 410 | 460 | 125 | 95 |

TABLE VI

| | | Cross Direction | | |
|---|---|---|---|---|
| Example | TS (g/2.5 cm) | E-B (%) | F-50% (g/2.5 cm) | RF-50% (g/2.5 cm) | R (%) |
| 10 | 1160 | 490 | | | |
| 11 | 1070 | 480 | | | |
| 12 | 380 | 450 | 65 | 23 | 90 |
| 13 | 970 | 450 | 135 | 58 | 90 |
| 14 | 1210 | 460 | 205 | 68 | 90 |
| 15 | 1700 | 460 | 270 | 95 | 90 |

As can be seen from the data in Tables V and VI, resins with different properties are processable into webs which have suitable properties and characteristics and may be more desirable for specific end use requirements.

EXAMPLES 16 AND 17

In Examples 16 and 17, nonwoven elastomeric microfiber webs were made as in Example 1 except that the thermoplastic elastomeric polyurethane polymer used was PS 455-208 and the polyurethane was blended with a hot melt acrylate-based cohesive resin, a copolymer at 95 weight percent isooctyl acrylate and 5 weight percent acrylic acid. In Example 16, 70 parts polyurethane were blended with 30 parts of the acrylate-based cohesive resin and, in Example 17, 50 parts polyurethane were blended with 50 parts of the acrylate-based cohesive resin. The fiber size, web basis weight, and web thickness are set forth in Table VII.

TABLE VII

| Example | Fiber size (microns) | Web basis weight (g/m2) | Web thickness (mm) |
|---|---|---|---|
| 16 | 22-30 | 45 | 0.20 |
| 17 | 22-30 | 48 | 0.21 |

The tensile strength (TS), elongation at break (E-B), force at 50% elongation (F-50%), recovery force at 50% elongation (RF-50%), and the percent recovery (R) were determined in both the machine direction and the cross direction. The results are set forth in Tables VIII and IX. The cohesive strength of the webs was also determined.

TABLE VIII

| Example | Machine Direction | | | | |
|---|---|---|---|---|---|
| | TS (g/2.5 cm) | E-B (%) | F-50% (g/2.5 cm) | RF-50% (g/2.5 cm) | R (%) |
| 16 | 1300 | 270 | 390 | 78 | 80 |
| 17 | 1100 | 225 | 370 | 72 | 70 |

TABLE IX

| Example | Machine Direction | | | | |
|---|---|---|---|---|---|
| | TS (g/2.5 cm) | E-B (%) | F-50% (g/2.5 cm) | RF-50% (g/2.5 cm) | R (%) |
| 16 | 580 | 240 | | | |
| 17 | 520 | 240 | | | |

The cohesive strength of the cohesive wraps of Examples 16 and 17 was about 200 g/2.5 cm and therefore independent of web construction.

EXAMPLES 18–31

In Example 18, an elastomeric cohesive wrap was prepared by coating one face of the nonwoven elastomeric microfiber web of Example 1 with a natural rubber-based latex cohesive material, GNL 200, 55% solids latex, available from Goodyear Rubber Co., at a coating weight of 18 g/m$^2$ using a knurled roll coater apparatus. After coating, the web was dried in a circulating air oven at 110° C. for about 3 minutes.

In Examples 19–23, elastomeric cohesive wraps were prepared as in Example 18 except the nonwoven microfiber webs used and the coating weight of the cohesive material were as set forth in Table X.

Each coated web was tested for cohesive strength. The results are set forth in Table X.

TABLE X

| Example | Web (Example) | Coating weight (g/m$_2$) | Cohesive strength (g/2.5 cm) |
|---|---|---|---|
| 18 | 1 | 18 | WF* |
| 19 | 6 | 20 | WF |
| 20 | 7 | 32 | WF |
| 21 | 10 | 16 | WF |
| 22 | 11 | 30 | WF |
| 23 | 12 | 34 | WF |

*Web failure

As can be seen from the data in Table X, the cohesive strength exceeds the web strengths at these coating weights.

EXAMPLES 24–31

In Example 24, an elastomeric cohesive wrap was prepared by coating both faces of the nonwoven elastomeric microfiber web of Example 1 with a natural rubber-based latex cohesive material, GNL 200, 55% solids latex, available from Goodyear Rubber Co., at a coating weight of 6 g/m$^2$ using a spray coater apparatus. After coating, the web was dried in a circulating air oven at 110° C. for about 1.5 minutes.

In Examples 25–30, elastomeric cohesive wraps were prepared as in Example 24, except the nonwoven microfiber webs used and the coating weight of the cohesive material were as set forth in Table XI.

In Example 31, an elastomeric cohesive wrap was prepared as in Example 24, except the cohesive material was a styrene-butadiene-based material, Tylac TM 97-698 available from Reichold Chemicals, Inc., Dover, Del., and the nonwoven microfiber web of Example 10 was used.

Each coated web was tested for cohesive strength. The results are set forth in Table XI.

TABLE XI

| Example | Web (Example) | Coating weight (g/m$^2$) | Cohesive strength (g/2.5 cm) |
|---|---|---|---|
| 24 | 1 | 6 | 370 |
| 25 | 7 | 8 | 360 |
| 26 | 7 | 10 | 460 |
| 27 | 10 | 5 | 300 |
| 28 | 10 | 8 | 370 |
| 29 | 11 | 9 | 390 |
| 30 | 11 | 13 | 520 |
| 31 | 10 | 6 | 190 |

As can be seen from the data in Table XI, suitable cohesive wrap can be made using various webs, adhesives, and adhesive coating weights.

EXAMPLES 32–36

In Example 32, an elastomeric adhesive dressing was prepared by coating one face of the elastomeric microfiber web of Example 12 with a 5 weight percent solution of polyvinyl carbamate and drying the coated web at 120° C. for 1.5 minutes to provide a low adhesion backsize (2 g/m$^2$) on the web and then coating a 22 weight percent solution of a copolymer of 97 parts isooctyl acrylate and 3 parts acrylamide onto a release liner (2060 BKG 157-168A, available from Daubert Coated Products, Dixon, Ill.) drying the coated adhesive in a circulating air oven at 40° C. for 1.0 minutes to obtain a semi-wet adhesive as taught in U.S. Pat. No. 3,121,021 (Copeland), laminating this adhesive onto the face of the web not bearing the low adhesion backsize coating, and then drying the laminate at 120° C. for 3 minutes.

In Examples 33 and 34, elastomeric adhesive dressings were prepared as in Example 32 except no low adhesion backsize coating was used and the web used was as set forth in Table XII.

In Examples 35 and 36, elastomeric adhesive dressings were prepared as in Example 32 except the adhesive was dried at 120° C. for 3 minutes to provide a dry adhesive which was applied to the elastomeric microfiber web as set forth in Table XII.

Each adhesive dressing was tested for adhesion to steel and to the low adhesion backsize coating using ASTM Test Method D-1000. The results are set forth in Table XII.

TABLE XII

| Example | Web (Example) | Coating weight (g/m$_2$) | Adhesion steel (g/2.5 cm) | Adhesion backing (g/2.5 cm) |
|---|---|---|---|---|
| 32 | 12 | 26 | 135 | 15 |
| 33 | 3 | 26 | 255[a] | WF[b] |
| 34 | 4 | 26 | 270[a] | WF |
| 35 | 12 | 25 | 254 | 26 |
| 36 | 13 | 25 | 251 | 23 |

[a] adhesive transfer
[b] web failure

As can be seen from the data in Table XII, elastic pressure-sensitive adhesive tapes can be prepared using the nonwoven elastomeric webs of the invention. As shown by the dressings of Examples 33 and 34, which do not have a low adhesion backsize coating, the low adhesion backsize coating is an integral part of the dressing where the dressing material is to be provided wound in a roll or supplied as a layered pack.

EXAMPLES 37–40

In Example 37, an elastomeric adhesive dressing was prepared by applying a low adhesion backsize coating on one face of the elastomeric microfiber web of Example 11 as in Example 32 and spray coating an adhesive solution containing 40 weight percent of a copolymer of 90 parts isooctyl acrylate and 10 parts acrylic acid onto the other face and drying the adhesive coated web at 105° C. for 3 minutes to provide an adhesive coating weight of 5 g/m$^2$.

In Example 38, an elastomeric adhesive dressing was prepared as in Example 37 except the adhesive coating was applied to achieve an adhesive coating weight of 8 g/m$^2$.

In Examples 39 and 40, elastomeric adhesive dressings were prepared as in Example 37 except in Example 39 the adhesive was a formulated block copolymer of 45 parts Kraton TM 1107, available from Shell Chemical Co. and 55 parts Wingtack TM resin, available from Goodyear Co., rapidly dissolved in toluene at 20 weight percent solids and in Example 40 the adhesive was 36-6053, a natural rubber adhesive available from National Adhesives Co.

Each adhesive dressing was tested for adhesion to steel and to the low adhesion backsize coating using ASTM Test Method D-1000. The results are set forth in Table XIII.

TABLE XIII

| Example | Web (Example) | Coating weight (g/m$_2$) | Adhesion steel (g/2.5 cm) | Adhesion backing (g/2.5 cm) |
|---|---|---|---|---|
| 37 | 11 | 5 | 35 | * |
| 38 | 11 | 8 | 42 | * |
| 39 | 11 | 8 | 24 | * |
| 40 | 11 | 8 | 16 | * |

*too low to obtain value

As can be seen from the data in Table XIII, pressure-sensitive adhesive dressings can be prepared using an adhesive spray process and that various types of adhesive are suitable for preparing the elastomeric adhesive dressings of the invention.

COMPARATIVE EXAMPLES 1–6

In Comparative Examples 1 and 2, polyurethane spunbond elastic webs commercially available under the tradename "Bondina" were tested for tensile strength and elongation at break in both the machine direction and in the cross direction.

In Comparative Examples 3 and 4, polyurethane spunbonded webs commercially available under the tradenames "Kanebo EA-50" and "Kanebo EA-75" were tested for tensile strength and elongation at break in both the machine direction and the cross direction.

In Comparative Examples 5, a melt blown microfiber web was prepared using Kraton TM G, an elastomeric styrenic-ethylene-butylene block copolymer available from Shell Chemical Company, Houston, Tex., as disclosed in U.S. Pat. No. 4,692,371 (Morman et al.) and tested for tensile strength and elongation at break in both the machine direction and the cross direction.

In Comparative Example 6, a melt blown microfiber web was prepared using a blend of 80 weight percent Kraton TM G and 20 weight percent polyethylene wax (PE Na601, available from U.S.I. Chemical Company) as disclosed in U.S. Pat. No. 4,663,220 (Wisneski et al.) and tested for tensile strength and elongation at break in both the machine direction and the cross direction.

The basis weight and fiber size for each web is set forth in Table XIV. The tensile strength and elongation at break for each comparative example are set forth in Table XV.

TABLE XIV

| Comparative Example | Basis weight (g/m$_2$) | Fiber size (microns) |
|---|---|---|
| 1 | 35 | 80+ |
| 2 | 62 | 80+ |
| 3 | 49 | 35–55 |
| 4 | 76 | 40–55 |
| 5 | 110 | 20–30 |
| 6 | 105 | 20–30 |

TABLE XV

| | Machine direction | | Cross direction | |
|---|---|---|---|---|
| Comparative Example | Tensile strength (g/2.5 cm) | Elongation at break (%) | Tensile strength (g/2.5 cm) | Elongation at break (%) |
| 1 | 625 | 310 | 185 | 360 |
| 2 | 1050 | 270 | 290 | 350 |
| 3 | 1500 | 380 | 450 | 400 |
| 4 | 2300 | 380 | 740 | 410 |
| 5 | 1200 | 850 | 420 | 950 |
| 6 | 675 | 750 | 200 | 900 |

As can be seen from the data in Table XV, the tensile strength in the machine direction is greater than 2½ times the tensile strength in the cross-direction in each example.

The various modifications and alterations of this invention will be apparent to those skilled in the rt without departing from the scope and spirit of this invention and this invention should not be restricted to that set forth herein for illustrative purposes.

What is claimed is:

1. A nonwoven elastomeric web comprising thermoplastic elastomeric melt blown small diameter fibers having a diameter of less than about 50 microns, the thermoplastic elastomeric small diameter fibers being selected from the group consisting of elastomeric polyurethanes, elastomeric polyesters, and elastomeric polyamides, and being randomly arrayed and bonded at points of contact such that the web has a machine direction tensile strength of at least about 30 g/2.5 cm width/g/m$^2$ basis weight, the tensile strength of the web in the direction of web formation is no greater than about 2.5 times the tensile strength of the web in the direction perpendicular to the direction of web formation, the web has multi-directional elastic properties, and the web recovers at least about 85% in the machine direction after being stretched 50%.

2. The nonwoven elastomeric web of claim 1 wherein the elastomeric small diameter fibers have diameters of from about 5 microns to about 30 microns.

3. The nonwoven elastomeric web of claim 1 wherein the basis weight of the nonwoven elastomeric web is in the range of from about 15 to about 150 grams/m$^2$.

4. The nonwoven elastomeric web of claim 1 wherein the web has an elongation at break of at least about 250%.

5. The nonwoven elastomeric web of claim 1 wherein the web has a machine direction force at 50% elongation of at least about 5 g/2.5 cm width/g/m$^2$ basis weight.

6. The nonwoven elastomeric web of claim 1 wherein the web has a recovery force at 50% elongation of at least about 1.2 g/2.5 cm width/g/m$^2$ basis weight.

7. The nonwoven elastomeric web of claim 1 wherein the web recovers at least about 80% in the cross direction after being stretched 50%.

8. An adhesive dressing comprising (1) a nonwoven elastomeric web having a first face and a second face comprising thermoplastic elastomeric melt blown small diameter fibers having a diameter of less than about 50 microns, the thermoplastic elastomeric small diameter fibers being selected from the group consisting of elastomeric polyurethanes, elastomeric polyesters, and elastomeric polyamides, and being randomly arrayed and bonded at points of contact such that the web has a machine direction tensile strength of at least about 30 g/2.5 cm width/g/m$^2$ basis weight, the tensile strength of the web in the direction of web formation is no greater than about 2.5 times the tensile strength of the web in a direction perpendicular to the direction of web formation, the web has multi-directional elastic properties, and the web recovers at least about 85% in the machine direction after being stretched 50%, (2) a pressure-sensitive adhesive on the first face of the web, and (3) a low adhesion backsize coating on the second face of the web.

9. An elastomeric cohesive wrap comprising (1) a nonwoven elastomeric web having a first face and a second face comprising thermoplastic elastomeric melt blown small diameter fibers having a diameter of less than about 50 microns, the thermoplastic elastomeric small diameter fibers being selected from the group consisting of elastomeric polyurethanes, elastomeric polyesters, and elastomeric polyamides, and being randomly arrayed and bonded at points of contact such that the web has a machine direction tensile strength of at least about 30 g/2.5 cm width/g/m$^2$ basis weight, the tensile strength of the web in the direction of web formation is no greater than about 2.5 times the tensile strength of the web in a direction perpendicular to the direction of web formation, the web has multi-directional elastic properties, and the web recovers at least about 85% in the machine direction after being stretched 50% and (2) a self-adhesive coating adhered to at least a one face of the web such that one portion of the web can adhere to another portion of the web.

10. The nonwoven elastomeric web of claim 1 wherein said thermoplastic elastomeric small diameter fibers are elastomeric polyurethanes.

* * * * *